(12) United States Patent
Srinivasan et al.

(10) Patent No.: US 8,562,807 B2
(45) Date of Patent: Oct. 22, 2013

(54) DROPLET ACTUATOR CONFIGURATIONS AND METHODS

(75) Inventors: Vijay Srinivasan, Durham, NC (US); Michael G. Pollack, Durham, NC (US); Zhishan Hua, Greensboro, NC (US); Arjun Sudarsan, Cary, NC (US); Allen E. Eckhardt, Durham, NC (US); Vamsee K. Pamula, Durham, NC (US)

(73) Assignee: Advanced Liquid Logic Inc., Research Triangle Park, NC (US)

( * ) Notice: Subject to any disclaimer, the term of this patent is extended or adjusted under 35 U.S.C. 154(b) by 222 days.

(21) Appl. No.: 12/747,231

(22) PCT Filed: Dec. 10, 2008

(86) PCT No.: PCT/US2008/086186
§ 371 (c)(1),
(2), (4) Date: Aug. 25, 2010

(87) PCT Pub. No.: WO2009/076414
PCT Pub. Date: Jun. 18, 2009

(65) Prior Publication Data
US 2010/0307917 A1    Dec. 9, 2010

Related U.S. Application Data

(60) Provisional application No. 61/012,567, filed on Dec. 10, 2007, provisional application No. 61/014,128, filed on Dec. 17, 2007, provisional application No. 61/092,709, filed on Aug. 28, 2008.

(51) Int. Cl.
*G01N 27/453* (2006.01)

(52) U.S. Cl.
USPC .................................................. 204/600

(58) Field of Classification Search
USPC .................................................. 204/400, 600
See application file for complete search history.

(56) References Cited

U.S. PATENT DOCUMENTS

| | | | |
|---|---|---|---|
| 6,565,727 B1 | 5/2003 | Shenderov | |
| 6,773,566 B2 | 8/2004 | Shenderov | |
| 6,911,132 B2 * | 6/2005 | Pamula et al. | 204/600 |
| 6,977,033 B2 | 12/2005 | Becker et al. | |

(Continued)

FOREIGN PATENT DOCUMENTS

| | | |
|---|---|---|
| JP | 2003112031 A | 4/2003 |
| WO | 2007120241 | 10/2007 |

(Continued)

OTHER PUBLICATIONS

Pollack et al., "Electrowetting-based actuation of droplets for integrated microfluidics," Lab Chip, 2002, 2, 96-101.*

(Continued)

*Primary Examiner* — Alex Noguerola
(74) *Attorney, Agent, or Firm* — William A. Barrett; Ward and Smith, P.A.

(57) ABSTRACT

Droplet actuators for conducting droplet operations, such as droplet transport and droplet dispensing, are provided. In one embodiment, the droplet actuator may include a substrate including, droplet operations electrodes arranged for conducting droplet operations on a surface of the substrate; and reference electrodes associated with the droplet operations electrodes and extending above the surface of the substrate. Other embodiments of droplet actuators and methods of loading and using such droplet actuators are also provided.

29 Claims, 13 Drawing Sheets

(56) References Cited

U.S. PATENT DOCUMENTS

| | | | |
|---|---|---|---|
| 7,052,244 | B2 | 5/2006 | Fouillet et al. |
| 7,163,612 | B2 | 1/2007 | Sterling et al. |
| 7,255,780 | B2 | 8/2007 | Shenderov |
| 7,328,979 | B2 | 2/2008 | Decre et al. |
| 7,439,014 | B2 | 10/2008 | Pamula et al. |
| 7,458,661 | B2 | 12/2008 | Kim et al. |
| 7,547,380 | B2 | 6/2009 | Velev |
| 7,641,779 | B2 | 1/2010 | Becker et al. |
| 7,727,466 | B2 | 6/2010 | Meathrel et al. |
| 7,901,947 | B2 | 3/2011 | Pollack et al. |
| 7,943,030 | B2 | 5/2011 | Shenderov |
| 8,093,064 | B2 | 1/2012 | Shah et al. |
| 2004/0055891 | A1 | 3/2004 | Pamula et al. |
| 2006/0124458 | A1 | 6/2006 | Nauber et al. |
| 2006/0194331 | A1* | 8/2006 | Pamula et al. ............... 436/150 |
| 2007/0023292 | A1 | 2/2007 | Kim et al. |
| 2007/0064990 | A1 | 3/2007 | Roth |
| 2007/0207513 | A1 | 9/2007 | Sorensen et al. |
| 2008/0098917 | A1 | 5/2008 | Rikihisa et al. |
| 2008/0124252 | A1 | 5/2008 | Marchand et al. |
| 2008/0151240 | A1 | 6/2008 | Roth |
| 2008/0274513 | A1 | 11/2008 | Shenderov |
| 2008/0283414 | A1 | 11/2008 | Monroe et al. |
| 2008/0305481 | A1 | 12/2008 | Whitman et al. |
| 2009/0192044 | A1 | 7/2009 | Fouillet et al. |
| 2009/0321262 | A1 | 12/2009 | Adachi et al. |
| 2010/0096266 | A1 | 4/2010 | Kim et al. |
| 2011/0118132 | A1 | 5/2011 | Winger et al. |
| 2011/0209998 | A1 | 9/2011 | Shenderov |
| 2012/0132528 | A1 | 5/2012 | Shenderov |

FOREIGN PATENT DOCUMENTS

| | | |
|---|---|---|
| WO | 2008098236 | 8/2008 |
| WO | 2008101194 | 8/2008 |
| WO | 2008134153 | 11/2008 |
| WO | 2009003184 | 12/2008 |
| WO | 2009021173 | 2/2009 |
| WO | 2010027894 | 3/2010 |

OTHER PUBLICATIONS

PCT International Search Report and Written Opinion for PCT/US2008/086186 dated May 27, 2009.

Tolun et al., "A Novel Fluorometric Enzyme Analysis Method for Hunter Syndrome Using Dried Blood Spots," Mol. Genet. Metab. (2012), doi:10.1016/j.ymgme.2001.12.011.

Wulff-Burchfield et al., "Microfluidic Platform Versus Conventional Real-Time Polymerase Chain Reaction for the Detection of Mycolpasma pneumoniae in Respiratory Specimens," Dignostic Microbology and Infectious Disease, 2010, vol. 67, pp. 22-29.

Xu et al., "Digital Microfluidic Biochip Design for Protein Crystallization," IEEE-NIH, 2007.

Yi et al, "Geometric Surface Modification of Nozzles for Complete Transfer of Liquid Drops," Solid-State Sensor, Actuators and Microsystems Workshop, Hilton Head Island, South Carolina, Jun. 6-10, 2004, pp. 164-167.

Yi et al, "Characterization of Electrowetting Acutation on Addressable Single-Side Coplanar Electrodes," J. Micromech. Microeng. 2006, vol. 16, pp. 2053-2059, http://dx.doi.org/10.1088/0960-1317/16/10/018.

Boles et al., "Droplet-Based Pyrosequencing Using Digital Microfluidics," Analytical Chemistry, vol. 83, pp. 8439-8447, Sep. 2011.

Dewey et al, "Towards a Visual Modeling Approach to Designing Microelectromechanical System Transducers," Journal of Micromechanics and Microengineering, vol. 9, pp. 332-340, Dec. 1999.

Dewey et al., "Visual Modeling and Design of Microelectromechanical System Transducers, " Microelectronics Journal, vol. 32, pp. 373-381, Apr. 2001.

Fair et al., "A Microwatt Metal Insulator Solution Transport (MIST) Device for Scalable Digital Biomicrofluidic Systems, " IEEE IEDM Technical Digest, pp. 16.4.1-16.4.4, 2001.

Fair et al., "Electrowetting-Based On-Chip Sample Processing for Integrated Microfluidics, " IEEE Int'l Electron Devices Meeting (IEDM), 2003.

Fair et al., "Chemical and Biological Applications of Digital Microfluidic Devices," IEEE Design and Test of Computers, vol. 24(1): pp. 10-24, Jan.-Feb. 2007.

Hua et al, "Multiplexed Real-Time Polymerase Chain Reaction on a Digital Microfluidic Platform," Analytical Chemistry, vol. 82, pp. 2310-2316, Mar. 2010.

Kleinert et al., "Dynamics and Stability of Oil Films During Droplet Transport by Electrowetting," 86th ACS Colloid & Surface Science Symposium, Jun. 13, 2012.

Millington et al., "Digital Microfluidics: A Future Technology in the Newborn Screening Laboratory?," Seminars in Perinatology, vol. 34, pp. 163-169, Apr. 2010.

Paik et al., "Rapid Droplet Mixers for Digital Microfluidic Systems," Lab on a Chip, vol. 3, pp. 253-259, 2003. (More mixing videos available, along with the article, at LOC's website.).

Paik et al., "Thermal Effects on Droplet Transport in Digital Microfluidics with Applications to Chip Cooling Processing for Integrated Microfluidics," Int'l Conf. on Thermal, Mechanics, and Thermomechanical Phenomena in Electronic Systems (ITherm), pp. 649-654, 2004.

Paik et al., "Droplet-Based Hot Spot Cooling Using Topless Digital Microfluidics on a Printed Circuit Board," Int'l Workshops on Thermal Investigations of ICs and Systems (THERMINIC), pp. 278-283, 2005.

Paik et al., "Adaptive Hot-Spot Cooling of Integrated Circuits Using Digital Microfluidics ," ASME Int'l Mechanical Engineering Congress and Exposition (IMECE), Nov. 5-11, 2005.

Paik et al., "Programmable Flow-Through Real-Time PCR Using Digital Microfluidics," 11th Int'l Conf. on Miniaturized Systems for Chemistry and Life Sciences, Paris, France, pp. 1559-1561, Oct. 7-11, 2007.

Paik et al., "Adaptive Cooling of Integrated Circuits Using Digital Microfluidics," accepted for publication in IEEE Transactions on VLSI Systems, 2007, and Artech House, Norwood, MA, 2007.

Paik et al, "A Digital-Microfluidic Approach to Chip Cooling," IEEE Design & Test of Computers, vol. 25, pp. 372-381, Jul. 2008.

Pamula et al., "Microfluidic Electrowetting-Based Droplet Mixing," Proceedings, MEMS Conf. Berkeley, pp. 8-10, Aug. 2001.

Pamula et al., "Cooling of Integrated Circuits Using Droplet-Based Microfluidics," Proc. ACM Great Lakes Symposium on VLSI, pp. 84-87, 2003.

Pamula et al., "A Droplet-Based Lab-on-a-Chip for Colorimetric Detection of Nitroaromatic Explosives," Proceedings of Micro Electro Mechanical Systems, pp. 722-725, 2005.

Pollack et al., "Electrowetting-Based Actuation of Liquid Droplets for Microfluidic Applications," Applied Physics Letters, vol. 77, No. 11, pp. 1725-1726, Sep. 11, 2000.

Pollack, M.G., "Electrowetting-Based Microactuation of Droplets for Digital Microfluidics," Ph.D. Thesis, Department of Electrical and Computer Engineering, Duke University, 2001.

Pollack et al., "Electrowetting-Based Microfluidics for High-Throughput Screening," SmallTalk 2001 Conf. Program Abstract, p. 149, San Diego, Aug. 2001.

Pollack et al., "Electrowetting-Based Actuation of Droplets for Integrated Microfluidics," Lab on a Chip (LOC), vol. 2, pp. 96-101, 2002.

Pollack et al., "Investigation of Electrowetting-Based Microfluidics for Real-Time PCR Applications," 7th Int'l Conf. on Micro Total Analysis Systems (μTAS), 2003.

Punnamaraju et al., "Voltage Control of Droplet Interface Bilayer Lipid Membrane Dimensions," Langmuir the Acs Journal of Surfaces and Colloids, vol. 27, Issue 2, pp. 618-626, 2011.

Ren et al., "Dynamics of Electro-Wetting Droplet Transport," Sensors and Actuators B (Chemical), vol. B87, No. 1, 201-6, 2002.

Ren et al., "Micro/Nano Liter Droplet Formation and Dispensing by Capacitance Metering and Electrowetting Actuation," IEEE-NANO, pp. 369-72, 2002.

(56) References Cited

OTHER PUBLICATIONS

Ren et al., "Automated Electrowetting-Based Droplet Dispensing with Good Reproducibility," Proc. Micro Total Analysis Systems (µTAS), pp. 993-996, 2003.

Schell et al., "Evaluation of a Digital Microfluidic real-time PCR Platform to detect DNA of *Candida albicans* in Blood," J. Clin Microbiol Infect Dis, Published on-line DOI 10.1007/s10096-012-15616, Feb. 2012.

Sista, R., "Development of a Digital Microfluidic Lab-on-a-Chip for Automated Immunoassay with Magnetically Responsive Beads, " Ph.D. Thesis, Dep't of Chemical Engineering, Florida State University, 2007.

Sista et al., "Heterogeneous Immunoassays Using Magnetic Beads on a Digital Microfluidic Platform," Lab on a Chip, vol. 8, pp. 2188-2196, Dec. 2008.

Sista et al., "Digital Microfluidic Platform for Multiplexing Enzyme Assays: Implications for Lysosomal Storage Disease Screening in Newborns," Clinical Chemistry, vol. 57, pp. 1444-1451, 2011.

Sista et al., "Rapid, Single-Step Assay for Hunter Syndrome in Dried Blood Spots Using Digital Microfluidics," Clinica Chimica Acta, vol. 412, pp. 1895-1897, 2011.

Srinivasan et al., "Scalable Macromodels for Microelectromechanical Systems," Technical Proc. 2001 Int'l Conf. on Modeling and Simulation of Microsystems, pp. 72-75, 2001.

Srinivasan et al., "A Digital Microfluidic Biosensor for Multianalyte Detection," Proc. IEEE 16th Annual Int'l Conf. on Micro Electro Mechanical Systems, pp. 327-330, 2003.

Srinivasan et al., "Clinical Diagnostics on Human Whole Blood, Plasma, Serum, Urine, Saliva, Sweat, and Tears on a Digital Microfluidic Platform," Proc. Micro Total Analysis Systems (µTAS), pp. 1287-1290, 2003.

Srinivasan et al., "3-D Imaging of Moving Droplets for Microfluidics Using Optical Coherence Tomography," Micro Total Analysis Systems (µTAS), pp. 1303-1306, 2003.

Srinivasan et al., "Droplet-Based Microfluidic Lab-on-a-Chip for Glucose Detection," Analytica Chimica Acta , vol. 507, No. 1, pp. 145-150, 2004.

Srinivasan et al., "An Integrated Digital Microfluidic Lab-on-a-Chip for Clinical Diagnostics on Human Physiological Fluids," Lab on a Chip, vol. 4, pp. 310-315, 2004.

Srinivasan et al., "Protein Stamping for MALDI Mass Spectrometry Using an Electrowetting-Based Microfluidic Platform," Lab-on-a-Chip: Platforms, Devices, and Applications, Conf. 5591, SPIE Optics East, Philadelphia, Oct. 25-28, 2004.

Srinivasan, V., "A Digital Microfluidic Lab-on-a-Chip for Clinical Diagnostic Applications," Ph.D. thesis, Dep't of Electrical and Computer Engineering, Duke University, 2005.

Su et al., "Yield Enhancement of Digital Microfluidics-Based Biochips Using Space Redundancy and Local Reconfiguration," Proc. Design, Automation and Test in Europe (DATE) Conf., pp. 1196-1201, 2005.

\* cited by examiner

DROPLET ACTUATOR CONFIGURATIONS AND METHODS

1 RELATED APPLICATIONS

In addition to the patent applications cited herein, each of which is incorporated herein by reference, this patent application is related to and claims priority to U.S. Provisional Patent Application No. 61/012,567, filed on Dec. 10, 2007, entitled "Droplet Actuator Loading by Displacement of Filler Fluid;" U.S. Provisional Patent Application No. 61/014,128, filed on Dec. 17, 2007, entitled "Electrode Configurations for a Droplet Actuator;" and U.S. Provisional Patent Application No. 61/092,709, filed on Aug. 28, 2008, entitled "Electrode Configurations for a Droplet Actuator;" the entire disclosures of which are incorporated herein by reference.

2 GRANT INFORMATION

This invention was made with government support under GM072155-02 and DK066956-02, both awarded by the National Institutes of Health of the United States. The United States Government has certain rights in the invention.

3 FIELD OF THE INVENTION

The invention relates to droplet actuators for conducting droplet operations, such as droplet transport and droplet dispensing, and to methods of loading and using such droplet actuators.

4 BACKGROUND OF THE INVENTION

Droplet actuators are used to conduct a wide variety of droplet operations, such as droplet transport and droplet dispensing. A droplet actuator typically includes a substrate with electrodes arranged for conducting droplet operations on a droplet operations surface of the substrate. Electrodes may include droplet operations electrodes and reference electrodes. Droplets subjected to droplet operations on a droplet actuator may, for example, be reagents and/or droplet fluids for conducting assays. There is a need for improved functionality when conducting droplet operations and for alternative approaches to configuring droplet actuators for conducting droplet operations.

There are various ways of loading reagents and droplet fluids into droplet actuators. Problems with such methods include the risk of introducing air into the fluid and the inability to reliably handle small droplet fluid volumes. Because of these and other problems, there is a need for alternative approaches to loading droplet fluids into a droplet actuator.

5 BRIEF DESCRIPTION OF THE INVENTION

The invention provides a droplet actuator. In one embodiment, the droplet actuator may include a substrate including, droplet operations electrodes arranged for conducting droplet operations on a surface of the substrate; and reference electrodes associated with the droplet operations electrodes and extending above the surface of the substrate.

In another embodiment the droplet actuator may include two substrates separated to form a gap. Droplet operations electrodes may be associated with at least one of the substrates and arranged for conducting droplet operations in the gap. Reference electrodes may be associated with at least one of the substrates and extending into the gap.

In yet another embodiment, the invention provides a droplet actuator including a substrate including droplet operations electrodes and reference electrodes configured for conducting droplet operations, wherein at least a subset of the reference electrodes is separated from a droplet operations surface by an insulator and/or dielectric material.

In still another embodiment, the invention provides a droplet actuator including two substrates separated to form a gap; droplet operations electrodes associated with at least one of the substrates and arranged for conducting droplet operations in the gap; and reference electrodes. The reference electrodes may be associated with at least one of the substrates; and separated from a droplet operations surface of the substrate by an insulator and/or a dielectric material.

Further, the invention provides a droplet actuator including a substrate, which may have droplet operations electrodes configured for conducting one or more droplet operations; and reference electrodes inset into and/or between and/or interdigitated with one or more droplet operations electrodes. A reference electrode may be inset into a droplet operations electrode. A reference electrode may be inset between two or more droplet operations electrodes. A reference electrode may be interdigitated with a droplet operations electrode.

The invention provides droplet operations electrodes that are rotationally but not reflectively symmetrical. These electrodes may be formed into paths and/or arrays. These electrodes are interdigitated. In some cases, these electrodes are not interdigitated. The rotational symmetry may in certain embodiments be X-fold, where X is 3, 4, 5, 6, 7, 8, 9, or 10. The rotational symmetry may in certain embodiments be X-fold, where X is greater than 10. In some cases, adjacent electrodes are arranged such that no straight line can be drawn between two adjacent electrodes without overlapping one or both of the two adjacent electrodes. In some cases, adjacent electrodes are not interdigitated but are arranged such that no straight line can be drawn between two adjacent electrodes without overlapping one or both of the two adjacent electrodes.

The invention also provides a droplet actuator including an electrode having a shape that comprises a section of a rotationally but not reflectively symmetrical shape, the electrode having X-fold rotational symmetry, where X is 5, 6, 7, 8, 9, 10 or more. A droplet actuator may include a path or array including one or more of such electrodes.

The invention provides a droplet actuator including top and bottom substrates separated to form a gap, each substrate including electrodes configured for conducting droplet operations, the gap arranged to provide a distance between the substrates sufficient to permit independent droplet operations on a droplet operations surface of each substrate. The top substrate may, in some embodiments, include an arrangement of electrodes that is substantially congruent with an arrangement of electrodes on the bottom substrate. The top substrate may, in some embodiments, include an arrangement of electrodes that is substantially congruent with and in registration with an arrangement of electrodes on the bottom substrate. In some embodiments, the gap is sufficiently wide that: one or more droplets having a footprint which is from about 1 to about 5 times the size of the footprint of a droplet operations electrode can be subjected to droplet operations on the droplet operations surface of the top substrate without contacting the droplet operations surface of the bottom substrate; and one or more droplets having a footprint which is from about 1 to about 5 times the size of the footprint of a droplet operations electrode can be subjected to droplet operations on the droplet operations surface of the bottom substrate without contacting the droplet operations surface of the top substrate.

The invention also provides a droplet actuator including: a first substrate including droplet operations electrodes configured for conducting one or more droplet operations; a second substrate including: a conductive layer at least partially contiguous with two or more of the droplet operations electrodes; and a perfluorophosphonate coating overlying at least a portion of the conductive layer. The first substrate and the second substrate are separated to form a gap for conducting droplet operations mediated by the droplet operations electrodes. The conductive layer may in some embodiments include indium tin oxide or a substitute therefor.

The invention further provides a droplet actuator including: two surfaces separated to form a gap; electrodes associated with one or more surfaces and arranged for conducting one or more droplet operations; a filler fluid in the gap; a reservoir including a droplet fluid in the reservoir; a fluid path from the reservoir into the gap; and optionally, an filler fluid opening arranged for permitting fluid to exit the gap and/or exit one portion of the gap into another portion of the gap; a pressure source configured to force dislocation of filler fluid in the gap and/or through the filler fluid opening and thereby force droplet fluid from the reservoir through the fluid path into the gap.

The pressure source may be configured such that the dislocation of filler fluid forces droplet fluid from the reservoir through the fluid path into the gap into sufficient proximity with one or more of the electrodes to enable one or more droplet operations to be mediated by the one or more of the electrodes. The pressure source may include a negative pressure source and/or a positive pressure source. In some cases, multiple reservoirs are provided, each arranged to permit a droplet fluid to be loaded into the gap. The droplet operation may, for example, include a droplet dispensing operation in which a droplet is dispensed from the droplet fluid.

The invention also provides a method of loading a droplet actuator, the method including providing: a droplet actuator loaded with a filler fluid; a reservoir including a droplet fluid; a fluid path extending from the reservoir into the droplet actuator; forcing filler fluid: from one locus in the droplet actuator to another locus in the droplet actuator; or out of the droplet actuator; thereby causing droplet fluid to flow through the fluid path and into the droplet actuator. Droplet fluid may be forced into sufficient proximity with one or more electrodes to enable one or more droplet operations to be mediated in the droplet actuator by the one or more electrodes. Filler fluid may be forced using a negative and/or positive pressure source. In some cases, multiple droplet fluids are loaded from multiple reservoirs. The droplet operation may, for example, include a droplet dispensing operation in which a droplet is dispensed from the droplet fluid.

The invention also provides a method of conducting a droplet operation on a droplet actuator, the method including: using a negative pressure to flow a source fluid into a droplet actuator gap into proximity with a droplet operations electrode; and using the droplet operations electrode along with other droplet operations electrodes to conduct the droplet operation. The droplet operation can include dispensing a droplet from the source fluid.

5.1 BRIEF DESCRIPTION OF THE FIGURES

Figure 9A:
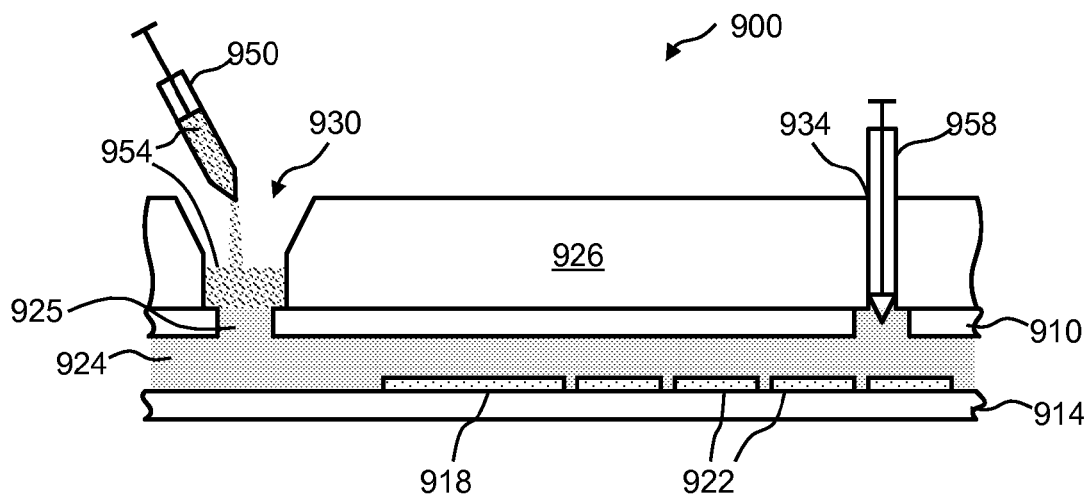
Figure 9B:
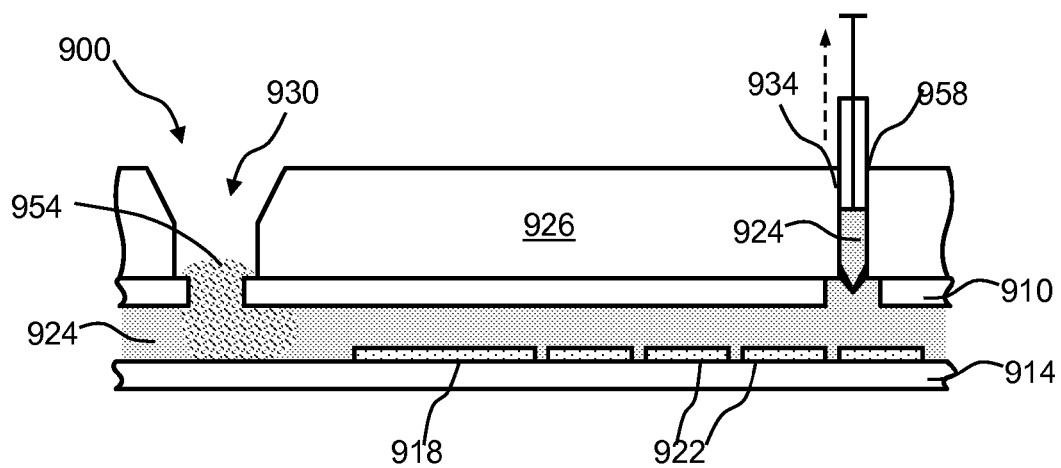
Figure 9C:
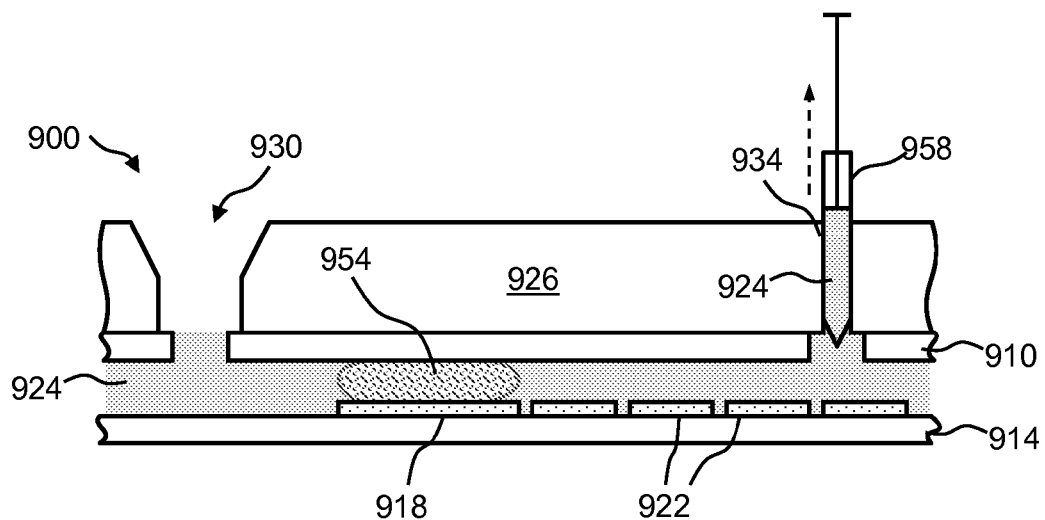

FIGS. 9A, 9B, and 9C illustrate a method of loading a droplet actuator using droplet fluid source and a negative pressure device.

Figure 10A:
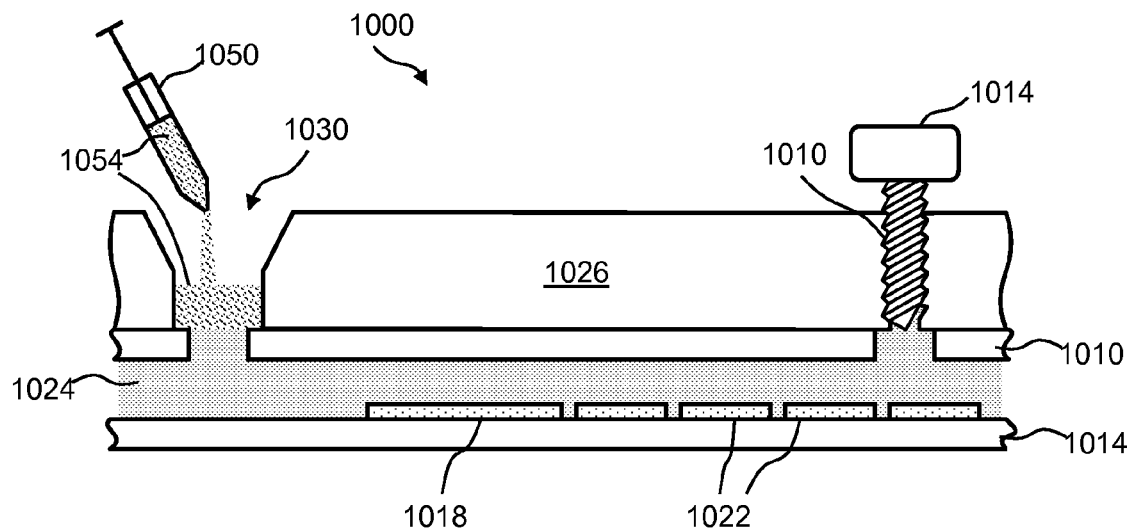
Figure 10B:
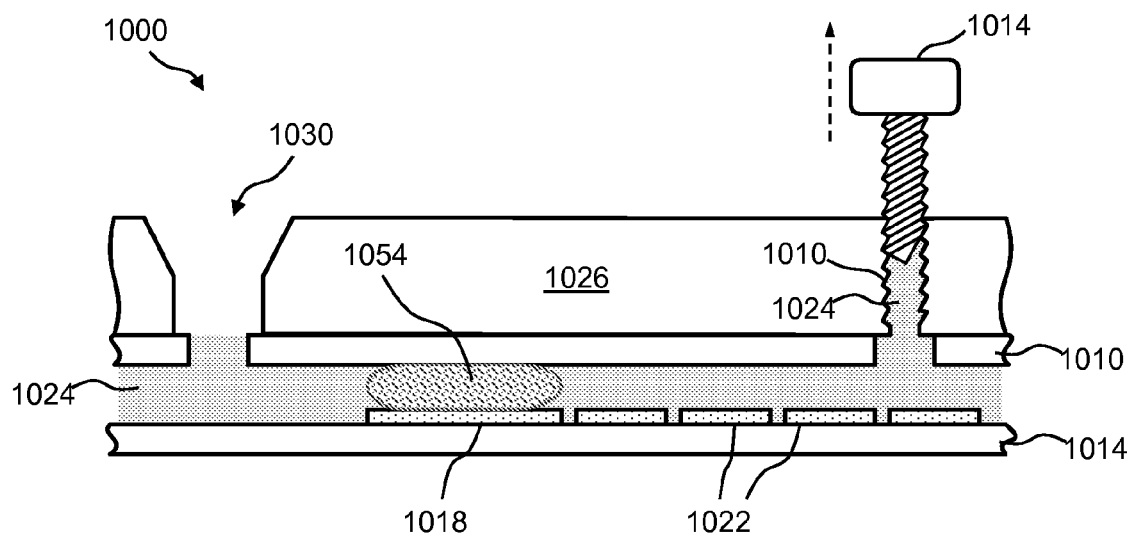

FIGS. 10A and 10B illustrate the use of a negative pressure device of loading assembly constituted by a threaded negative pressure opening with a screw.

Figure 11A:
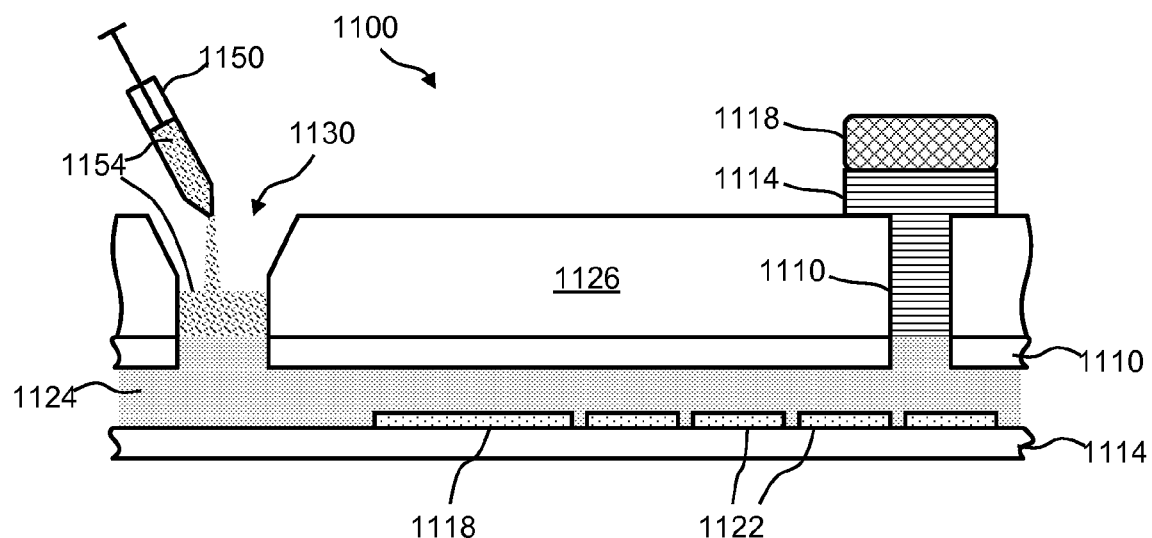
Figure 11B:
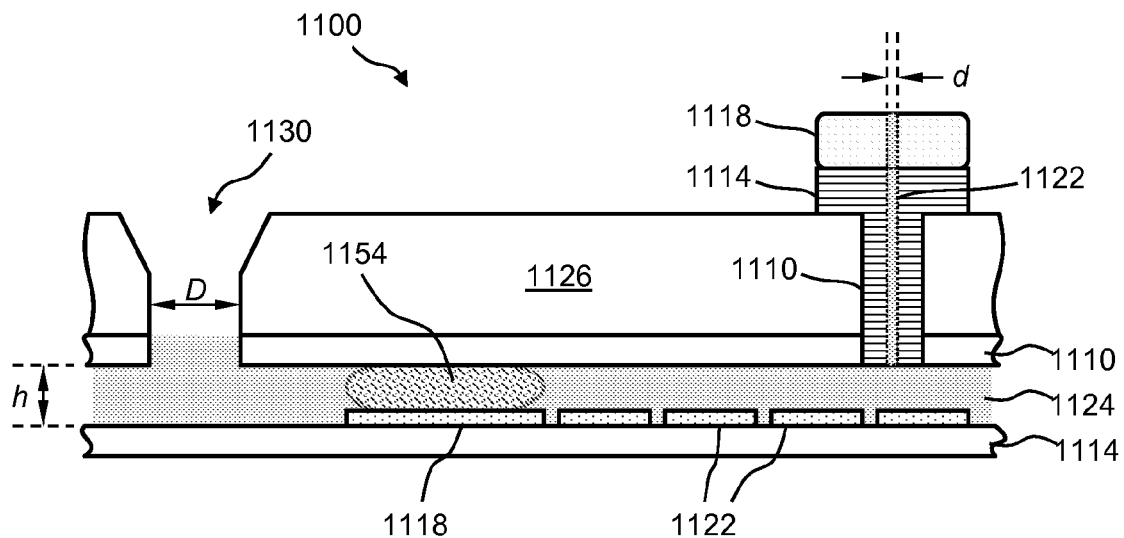

FIGS. 11A and 11B illustrate FIG. 11A a negative pressure loading implementation similar to those described in FIGS. 8 and 9, except that the negative pressure opening and the negative pressure device of the loading assembly is replaced with a negative pressure opening that includes a septum and an absorbent material.

Figure 12A:
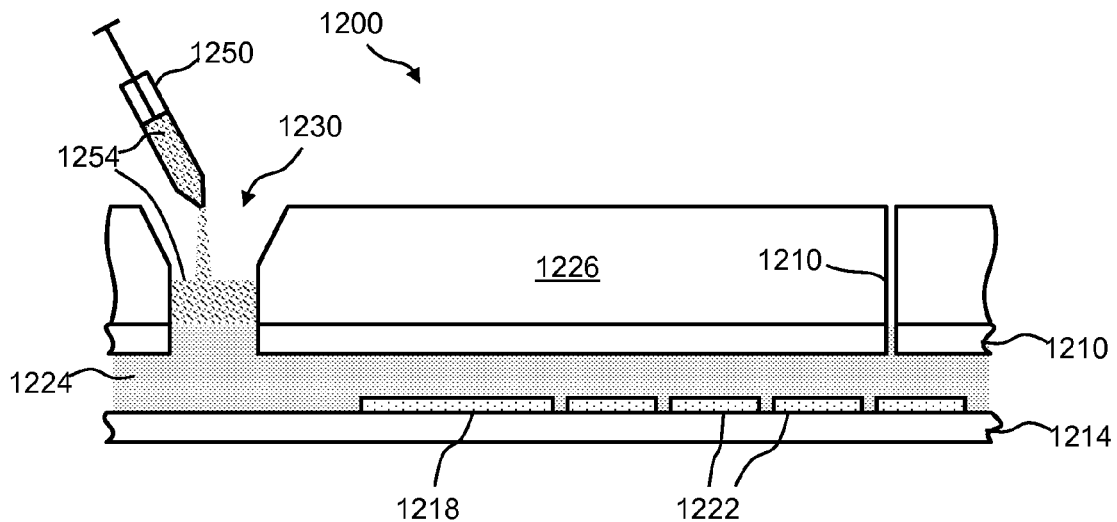
Figure 12B:
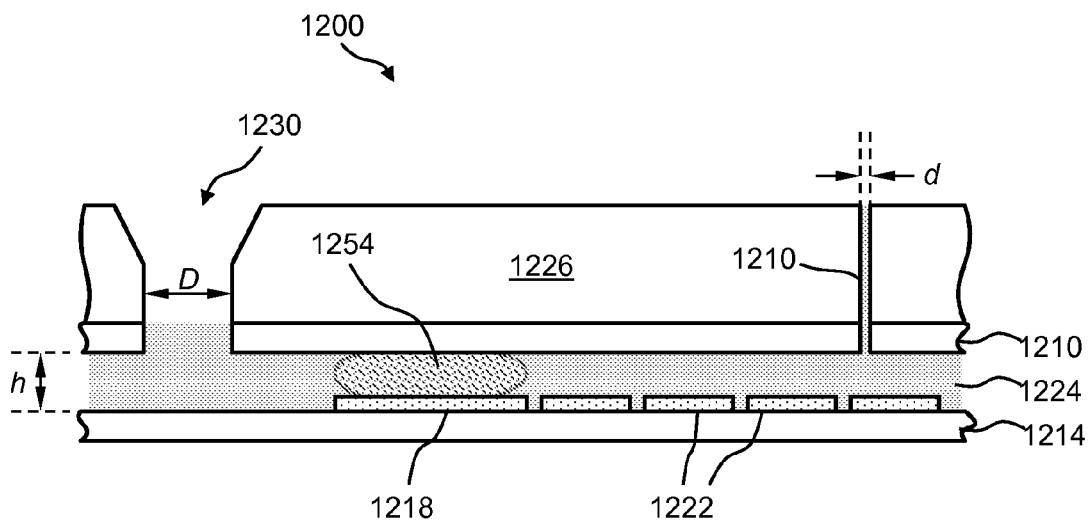

FIGS. 12A and 12B illustrate side views of a droplet actuator that uses a capillary as a negative pressure opening.

Figure 13A:
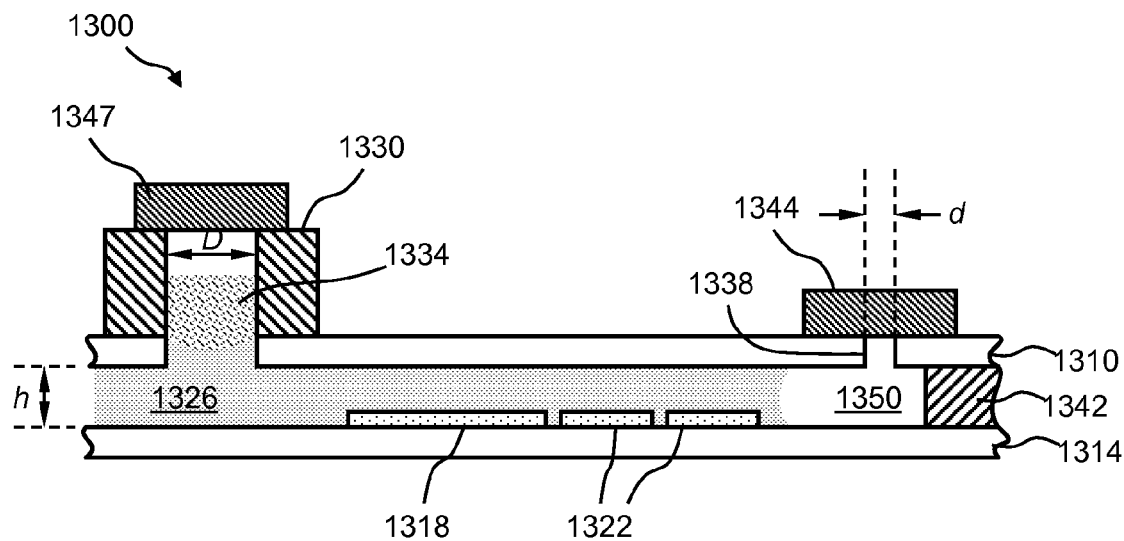
Figure 13B:
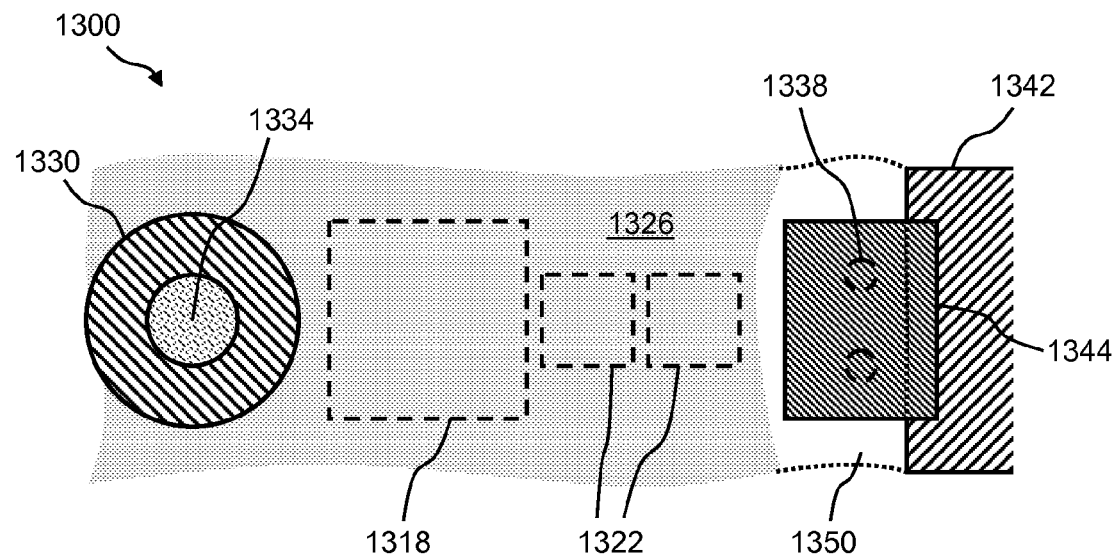

FIGS. 13A and 13B illustrate a side view and top view, respectively, of a droplet actuator with sealed vent holes.

6 DEFINITIONS

As used herein, the following terms have the meanings indicated.

"Activate" with reference to one or more electrodes means effecting a change in the electrical state of the one or more electrodes which in the presence of a droplet results in a droplet operation.

"Droplet" means a volume of liquid on a droplet actuator that is at least partially bounded by filler fluid. For example, a droplet may be completely surrounded by filler fluid or may be bounded by filler fluid and one or more surfaces of the droplet actuator. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet actuator.

"Droplet Actuator" means a device for manipulating droplets. For examples of droplets, see U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on filed on Jan. 30, 2006; U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000, both to Shenderov et al.; Pollack et al., International Patent Application No. PCT/US2006/047486, entitled "Droplet-Based Biochemistry," filed on Dec. 11, 2006, the disclosures of which are incorporated herein by reference. Methods of the invention may be executed using droplet actuator systems, e.g., as described in International Patent Application No. PCT/US2007/009379, entitled "Droplet manipulation systems," filed on May 9, 2007. In various embodiments, the manipulation of droplets by a droplet actuator may be electrode mediated, e.g., electrowetting mediated or dielectrophoresis mediated.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; condensing a droplet from a vapor; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to size of the resulting droplets (i.e., the size of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. In various embodiments, the droplet operations may be electrode mediated, e.g., electrowetting mediated or dielectrophoresis mediated.

"Filler fluid" means a fluid associated with a droplet operations substrate of a droplet actuator, which fluid is sufficiently immiscible with a droplet phase to render the droplet phase subject to electrode-mediated droplet operations. The filler fluid may, for example, be a low-viscosity oil, such as silicone oil. Other examples of filler fluids are provided in International Patent Application No. PCT/US2006/047486, entitled, "Droplet-Based Biochemistry," filed on Dec. 11, 2006; and in International Patent Application No. PCT/US2008/072604, entitled "Use of additives for enhancing droplet actuation," filed on Aug. 8, 2008.

The terms "top" and "bottom" are used throughout the description with reference to the top and bottom substrates of the droplet actuator for convenience only, since the droplet actuator is functional regardless of its position in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

7 DETAILED DESCRIPTION OF THE INVENTION

The invention provides modified droplet actuators, as well as methods of making and using such droplet actuators. Among other things, the droplet actuators and methods of the invention provide improved functionality when conducting droplet operations and alternative approaches to configuring droplet actuators for conducting droplet operations. The invention also provides improved loading configurations for droplet actuators, as well as improved methods of loading droplet actuators, and reliable handling small droplet fluid volumes.

Figure 1:
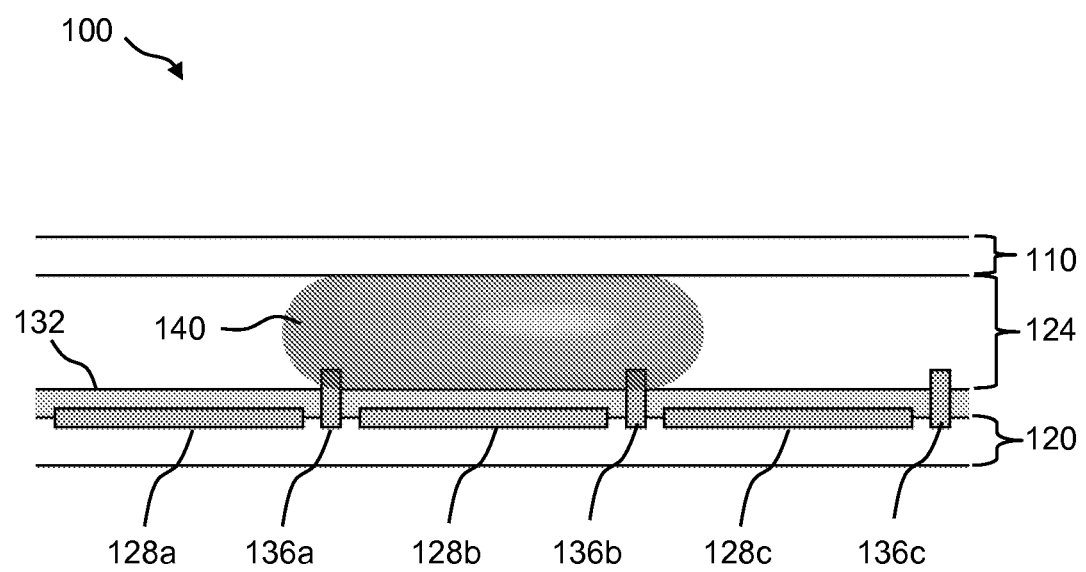
FIG. 1 illustrates a side view of a section of a droplet actuator including a top substrate and a bottom substrate that are separated to form a gap therebetween, and including reference electrodes provided as exposed posts or pillars that protrude through insulator layer and into the gap.

FIG. 1 illustrates a side view of a section of droplet actuator 100. Droplet actuator 100 includes a top substrate 110 and a bottom substrate 120 that are separated to form a gap 124 therebetween. The top substrate may or may not be present. A set of droplet operations electrodes 128, e.g., electrodes 128a, 128b, and 128c, are associated with bottom substrate 120. In one embodiment, the droplet operations electrodes comprise electrowetting electrodes. An insulator layer 132 is provided atop bottom substrate 120 and electrodes 128. Insulator layer 132 may be formed of any dielectric material, such as polyimide. Additionally, a set of reference electrodes 136 (e.g., reference electrodes 136a, 136b, and 136c) are arranged between electrodes 128, as shown in FIG. 1. A hydrophobic layer (not shown) may be disposed atop insulator layer 132.

Reference electrodes 136 are provided as exposed posts or pillars that protrude through insulator layer 132 and into gap 124 where the reference electrodes may contact the droplet 140. The function of the reference electrodes 136 is to bias droplet 140 at the ground potential or another reference potential. The reference potential may, for example, be a ground potential, a nominal potential, or another potential that is different than the actuation potential applied to the droplet operations electrodes. In a related embodiment, the tops of reference electrodes 136 are substantially flush the insulator layer 132. In another related embodiment, the tops of reference electrodes 136 are substantially flush with the hydrophobic layer (not shown). In yet another related embodiment, the tops of reference electrodes 136 are substantially flush with insulator layer 132, and the hydrophobic layer (not shown) overlies the tops of reference electrodes 136. Further, in another related embodiment, the tops of reference electrodes 136 lie within insulator layer 132 but below a top surface of insulator layer 132, e.g., as illustrated in FIG. 2.

Figure 2:
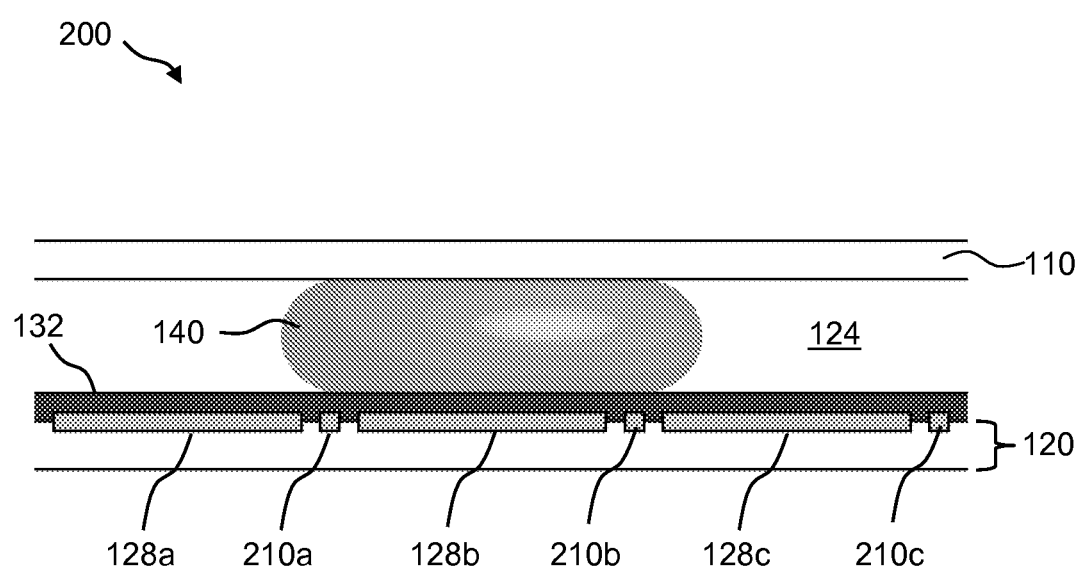
FIG. 2 illustrates a side view of a section of droplet actuator that is substantially the same as the droplet actuator shown in FIG. 1, except that reference electrodes that protrude through the insulator layer are replaced with reference electrodes that extend into but do not protrude through insulator layer.

FIG. 2 illustrates a side view of a section of droplet actuator 200. Droplet actuator 200 is substantially the same as droplet actuator 100 of FIG. 1, except that reference electrodes 136 of droplet actuator 100 that protrude through insulator layer 132 are replaced with reference electrodes 210 (e.g., reference electrodes 210*a*, 210*b*, and 210*c*) that extend into but do not protrude through insulator layer 132. The inventors have unexpectedly found that droplet operations can be conducted using insulated reference electrodes by inducing a voltage in the droplet (e.g., by fringing fields). Using insulated reference electrodes has the advantage that the device is easier to manufacture (e.g., no patterning of the insulator layer 132 is required).

In one embodiment of FIG. 2, the top substrate 110 may include a conductive coating (not shown) over some portion or all of the surface exposed to the droplet actuator. An example of such a conductive coating is indium tin oxide (ITO). The conductive coating may be electrically connected to reference electrode 210 through a resistor or a capacitor. The capacitor may be formed between the conductive coating and reference electrode 210 (serving as the plates of the capacitor) with the insulator layer 132 and as the gap 124 serving as a composite dielectric. In one embodiment, portions of the reference electrode 210 are not covered with the insulator 132. In another embodiment, portions of the reference electrode 210 are not covered with the insulator 132 and protrude through the substrate as shown in FIG. 1. In yet another embodiment, the insulated reference electrodes may be provided on the top substrate 110, e.g., as illustrated in FIG. 3.

Figure 3:
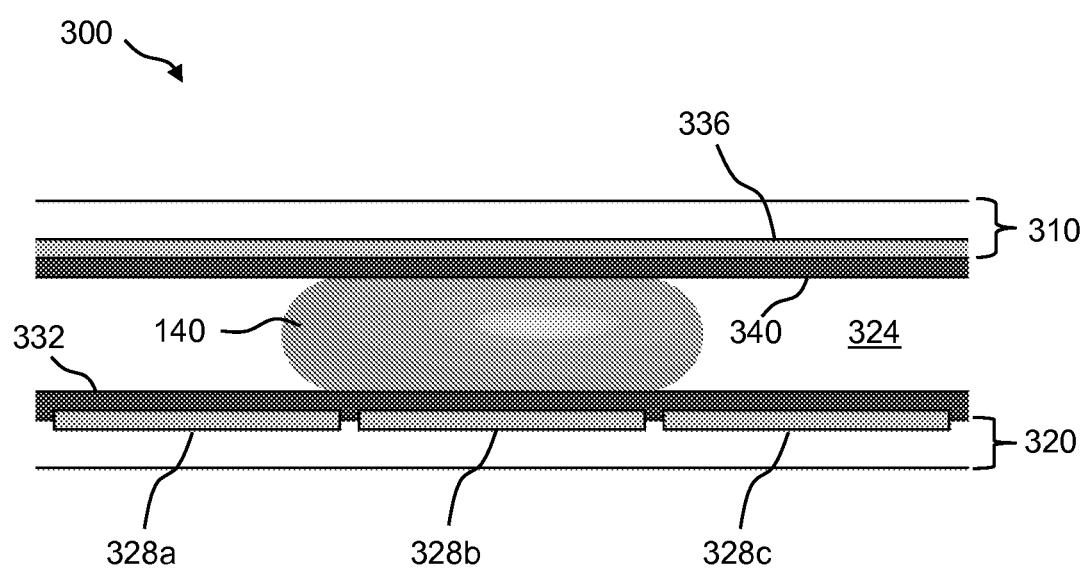
FIG. 3 illustrates a side view of a section of a droplet actuator that includes a top substrate and a bottom substrate that are arranged having a gap therebetween, and including a reference electrode associated with the top substrate atop which is provided an insulator layer.

FIG. 3 illustrates a side view of a section of droplet actuator 300. Droplet actuator 300 includes a top substrate 310 and a bottom substrate 320 that are arranged having a gap 324 therebetween. A set of electrodes 328 (e.g., electrodes 328*a*, 328*b*, and 328*c*) are associated with bottom substrate 320. An insulator layer 332 is provided atop bottom substrate 320 and electrodes 328. Additionally, a reference electrode 336 is associated with top substrate 310 atop which is provided an insulator layer 340. Insulator layers 332 and 340 may be formed of any dielectric material, such as polyimide. A hydrophobic coating (not shown) may be disposed on the surface of the insulator exposed to the gap. In certain embodiments the thickness of insulator 332 is larger than the thickness of insulator 340 by for example a factor of 2, 3, 4, 5, 10, 25, 50, 100. The factor need not be an integer and can be fractions. The larger the factor the lower the voltage required for droplet operations. Embodiments shown in FIG. 2 and FIG. 3 can also be combined to result in a device with reference electrodes on both substrates. The reference elements may be electrically connected to each other through a resistor or a capacitor. The capacitor may be formed between the two reference electrodes (serving as the plates of the capacitor) with the insulator layer 332 and as the gap 324 serving as a composite dielectric.

As noted with respect to droplet actuator 200 of FIG. 2, the inventors have unexpectedly found that droplet operations can be conducted using insulated reference electrodes by inducing a voltage in the droplet.

In one embodiment, the dielectric material is a hydrophobic material. For example, fluorinated ethylene propylene (FEP; available from DuPont as Teflon® FEP) is a suitable hydrophobic material. The hydrophobic material may, in some embodiments, serve as both the dielectric and the hydrophobic coating. This embodiment improves ease of manufacture, since an additional hydrophobic coating is not required. In a related embodiment, the dielectric material includes a laminated film. FEP also serves as an example of a laminated film. Using a film dielectric which is hydrophobic facilitates use perfluorinated solvents as filler fluids. Perfluorinated solvents are ideal filler fluids for many applications, since they are immiscible with both aqueous and organic liquids. Thus, aqueous and organic droplets can be subjected to droplet operations in such an environment.

Thus, the invention also provides a method of conducting a droplet operation on an organic droplet in a droplet actuator loaded with perfluorinated solvent as a filler fluid. For example, the method provides for dispensing one or more organic droplets from a source organic droplet; splitting, separating or dividing an organic droplet into two or more organic droplets; transporting an organic droplet from one location to another in any direction; merging or combining two or more organic droplets into a single droplet; diluting an organic droplet; mixing an organic droplet; agitating an organic droplet; deforming an organic droplet; retaining an organic droplet in position; incubating an organic droplet; heating an organic droplet; vaporizing an organic droplet; condensing an organic droplet from a vapor; cooling an organic droplet; disposing of an organic droplet; transporting an organic droplet out of a droplet actuator; other droplet operations described herein; and/or any combination of the foregoing; in each case on a droplet actuator in which the droplet operations surface is coated with, in contact with or flooded with a perfluorinated solvent. The foregoing operations are suitably conducted on a droplet operations surface that is composed of or is coated with a hydrophobic perfluorinated solvent-tolerant coating, such as FEP.

Figure 4A:
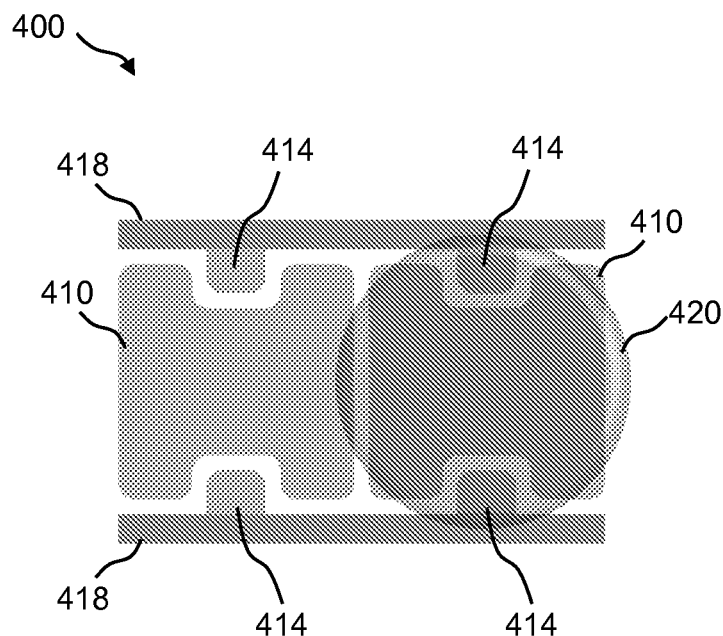
FIG. 4A illustrates an electrode pattern for a droplet actuator, including electrodes which are substantially H-shaped, leaving gaps in top and bottom regions for reference electrodes.

FIG. 4A illustrates an electrode pattern 400 for a droplet actuator (not shown). Droplet actuator 400 includes a set of electrodes 410. Electrodes 410 are substantially H-shaped, leaving gaps in top and bottom regions for references electrodes 414. Reference electrodes 414 are inset into the gaps in electrodes 410. As shown, gaps are provided on two sides of electrodes 410; however in some embodiments, gaps may be provided on only one side or on more than two sides. Further, the illustrated electrodes show single gaps with single reference electrodes inset therein; however, it will be appreciated that multiple gaps may be provided, and in some embodiments, the electrode 410 and the reference electrode 414 may be substantially interdigitated. Electrodes 410 may be used to conduct one or more droplet operations.

Reference electrodes 414 may be exposed to the gap, and in some cases, they may protrude into the gap, e.g., as described with reference to reference electrodes 136 of FIG. 1 or they may be insulated, e.g., as described with reference to FIGS. 2 and 3. One or more insulated wires 418 provide an electrical connection to reference electrodes 414. FIG. 4A shows a droplet 420 that is being manipulated along electrodes 410 using reference electrodes 414.

In one embodiment, the top or bottom substrate may include a conductive coating over some portion or all of the surface exposed to the droplet actuator. An example of such a conductive coating is indium tin oxide (ITO). The conductive coating may itself be coated with a hydrophobic layer. A variety of materials are suitable for coating the conductive layer to provide a hydrophobic surface. One example is a class of compounds known as perfluorophosphonates. Perfluorophosphonates may be useful for establishing a hydrophobic layer over a conductive layer, such as a metal. In one embodiment, a perfluorophosphonate is used to form a substantial monolayer over the conductive layer.

For example, a droplet actuator may include a metal conducting layer coated with a perfluorophosphonate exposed to a region in which droplets are subjected to droplet operations. Similarly, a droplet actuator may include a metal conducting layer coated with a perfluorophosphonate monolayer exposed to a region in which droplets are subjected to droplet operations. The perfluorophosphonate may be deposited on the conducting layer in an amount which facilitates the conducting of droplet operations. The perfluorophosphonate layer may reduce fouling during droplet operations relative to fouling that would occur in the absence of the phosphonate or perfluorophosphonate coating. The conducting layer may, in some embodiments, include ITO.

As another example, a droplet actuator comprising two substrates separated to form a gap, each substrate comprising electrodes configured for conducting droplet operations, may include ITO on a top substrate coated with a perfluorophosphonate.

A suitable perfluorophosphonate for use in accordance with the invention is 1-phosphonoheptadecafluorooctane ($CF_3(CF_2)_7PO_3H_2$). This material can be synthesized using known methods starting with 1-bromoheptadecafluorooctane ($CF_3(CF_2)_7Br$). Similar molecules of varying lengths can be synthesized using well-known techniques starting with known precursors.

Figure 4B:
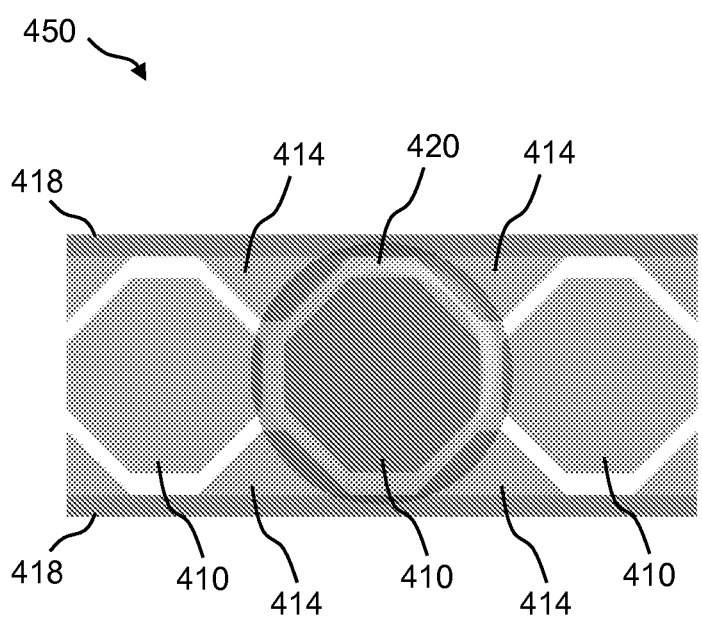
FIG. 4B illustrates an electrode pattern in which electrodes are shaped to provide a gap between each adjacent pair of electrodes, and reference electrodes are inset between electrodes rather than inset into electrodes as shown in (FIG. 4A).

FIG. 4B illustrates an electrode pattern 450 for a droplet actuator (not shown). Droplet actuator 450 is substantially the same as droplet actuator 400 of FIG. 4A, except that the geometries of electrodes 410 and the inset reference electrodes 414 differ from the electrode geometries illustrated in FIG. 4A. Electrodes 410 in FIG. 4B are shaped to provide a gap between each adjacent pair of electrodes 410. Electrodes 414 are inset between electrodes 410 rather than inset into electrodes 410.

As described above with reference to FIG. 1A, reference electrodes 414 in FIG. 4B may also be exposed to the gap, and in some cases, they may protrude into the gap, e.g., as described with reference to reference electrodes 136 of FIG. 1 or they may be insulated, e.g., as described with reference to FIGS. 2 and 3. One or more insulated wires 418 provide an electrical connection to reference electrodes 414. FIG. 4B shows a droplet 420 that is being manipulated along electrodes 410 using reference electrodes 414. Electrodes 410 may be used to conduct one or more droplet operations.

FIGS. 5A, 5B, 5C, 5D and 5E illustrate electrode patterns 510, 520, 530, 540, and 550, respectively, which are yet other nonlimiting examples of electrode configurations of the invention. Electrode patterns 510, 520, 530, 540, and 550 illustrate configurations in which the electrodes are overlapping, but not interdigitated, in order to facilitate droplet overlap with adjacent electrodes. These electrode patterns can be combined with reference electrodes that are also inset into and/or between and/or interdigitated with the electrodes, e.g., as described with reference to FIG. 4. The illustrated overlapping electrodes exhibit rotational symmetry. The examples illustrated in FIG. 5 show four-fold rotational symmetry, but it will be appreciated that the overlapping electrodes may exhibit a rotational symmetry which is X-fold, where X is 3, 4, 5, 6, 7, 8, 9, 10 or greater. Further, a droplet actuator may combine electrodes with different X-fold rotational symmetries.

Electrodes with rotational symmetry are preferred for overlapping electrodes, since the symmetry causes the droplets to be centered over the electrode. Further, the droplet shape will also have rotational symmetry, which permits overlap with adjacent electrodes or reference elements in all directions. In some embodiments, one or more of the electrodes have rotational symmetry but not reflection symmetry. In another embodiment, one or more of the electrodes have rotational symmetry and reflection symmetry, where the rotational symmetry is X-fold, and X is 5, 6, 7, 8, 9, 10 or more. In a further embodiment, the rotationally symmetrical overlapping electrodes are arranged such that no straight line can be drawn between two adjacent electrodes without overlapping one or both of the two adjacent electrodes. The invention also includes electrodes that are sections of rotationally symmetrical shapes, such as a quarter or half of a rotationally symmetrical shape. In some embodiments, the sections are characterized in that the lines creating the sections generally intersect the center point of the rotationally symmetrical shape, i.e., like slices of a pie. In still another embodiment, the overlapping regions of adjacent rotationally symmetrical electrodes generally fit together like pieces of a puzzle except that each point along adjacent edges of adjacent electrodes is separated by a gap from a corresponding point on the other of the adjacent electrodes.

Figure 6:
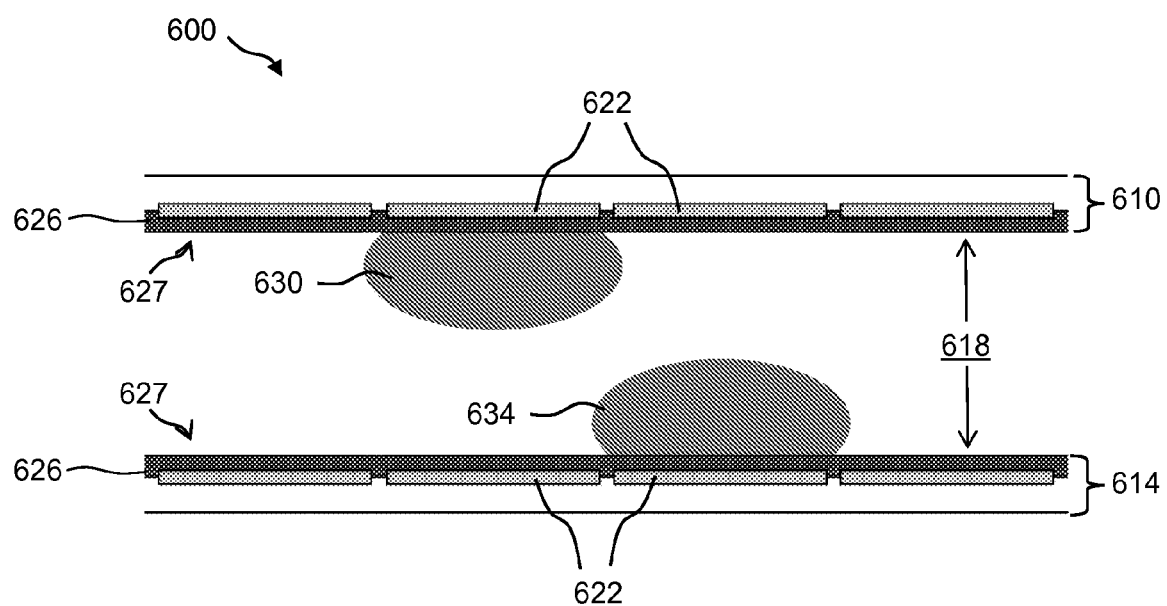
FIG. 6 illustrates a side view of a droplet actuator in which droplets may be subjected to droplet operations along both substrates (top and bottom).

FIG. 6 illustrates a side view of a droplet actuator 600. Droplet actuator 600 includes a top substrate 610 and a bottom substrate 614 that are arranged in a generally parallel fashion. Top substrate 610 and bottom substrate 614 are separated to provide a gap 618 therebetween. Both top substrate 610 and bottom substrate 614 include a set of electrodes 622, e.g., droplet operations electrodes. In the embodiment shown, both substrates include an insulator layer 626 associated therewith, which forms a droplet operations surface 627. Insulator layers 626 may be formed of any dielectric material, such as polyimide. Reference electrodes are not shown. A hydrophobic coating (not shown) may also be present.

In one embodiment, droplet operations electrodes 622 include at least a subset of electrodes 622 associated with top substrate 610 which are substantially congruent (having substantially the same size and shape) with and/or in registration (being substantially aligned on opposite plates) with a subset of electrodes 622 associated with bottom substrate 614 (e.g., a perpendicular line passing through the center-point of an electrode 622 on the bottom substrate 614 would approximately pass through the center point of a corresponding electrode 622 on the top substrate 610).

In one embodiment, gap 618 is sufficiently wide that: (a) one or more droplets 630 having a footprint which is from about 1 to about 5 times the size of the footprint of a droplet operations electrode 622 can be subjected to droplet operations on surface 627 of top substrate 610 without contacting surface 627 of bottom substrate 614; and (b) one or more droplets 634 having a footprint which is from about 1 to about 5 times the size of the footprint of a droplet operations electrode 622 can be subjected to droplet operations on surface 627 of bottom substrate 614 without contacting surface 627 of top substrate 610.

In this embodiment, droplets may be subjected to droplet operations along both substrates (top and bottom). In one embodiment, droplets may be merged by bringing a droplet on one surface into contact with a droplet on the other surface.

Droplet actuator cartridges of the invention may in various embodiments include fluidic inputs, on-chip reservoirs, droplet generation units and droplet pathways for transport, mixing, and incubation.

The fluidic input port provides an interface between the exterior and interior of the droplet actuator. The design of the fluidic input port is challenging due to the discrepancy in the scales of real world samples (microliters-milliliters) and the lab-on-a-chip (sub-microliter). If oil is used as the filler fluid in the droplet actuator gap, there is also the possibility of introducing air bubbles during liquid injection. The dimensions of the fluidic input may be selected to ensure that the liquid is stable in the reservoirs and does not spontaneously flow back to the loading port after loading. The entrapment of air as bubbles in the filler fluid should be completely avoided or minimized during the loading process.

In some embodiments the fluidic input port is designed for manual loading of the reservoirs using a pipette through a substrate of the droplet actuator. The sample (or reagent) may, for example, be injected into the reservoir through a loading opening in the top substrate. The opening may, for example, be configured to fit a small volume (<2 µL) pipette tip.

Figure 7:
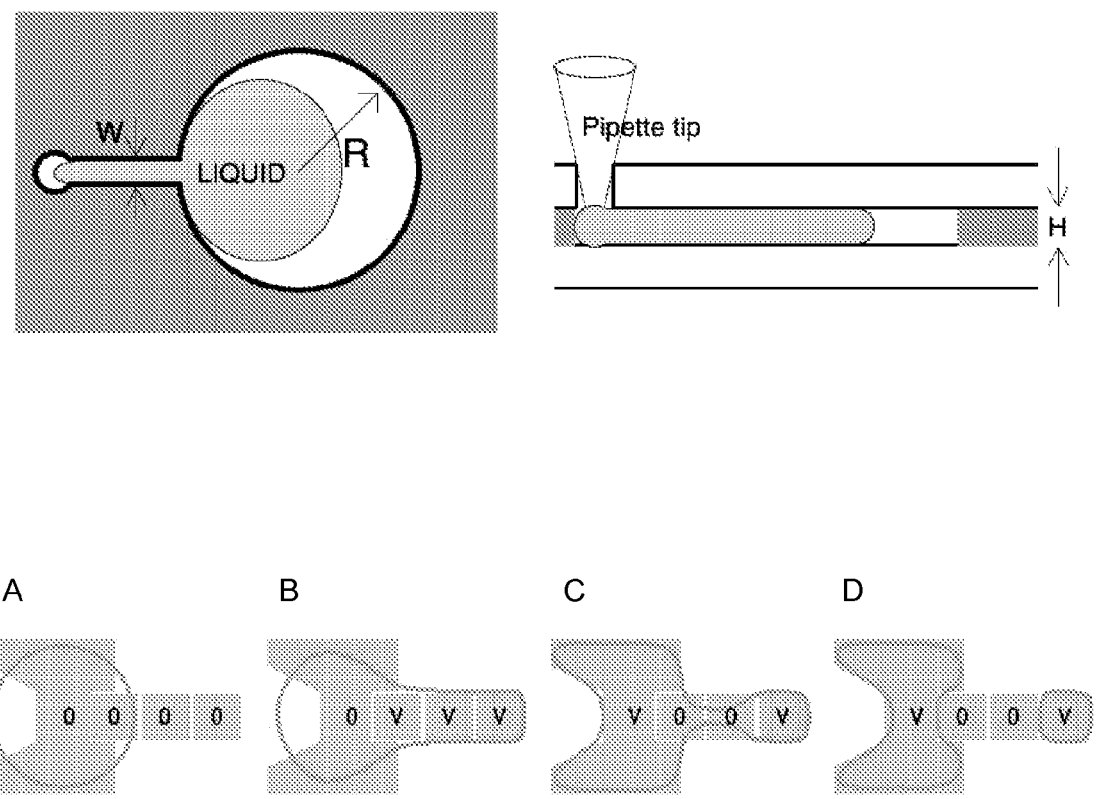
FIG. 7 illustrates an embodiment in which the loading opening is connected to the reservoir by a narrow channel of width w, patterned in the spacer material.

FIG. 7 illustrates an embodiment in which the loading opening is connected to the reservoir by a narrow channel of width w, patterned in the spacer material. The liquid pressure in the reservoir is on the order of $\gamma(1/R+1/H)$ where R is the radius of the reservoir, H is the height of the reservoir and $\gamma$ is the interfacial tension of the liquid with the surrounding media. Since R is typically much greater than h the pressure can be approximated as $\gamma/H$. The pressure in the channel connecting the loading port and the reservoir is $\gamma(1/w+1/H)$. If w is on the order of H then the pressure in the channel is $2\gamma/H$ which is twice the pressure in the reservoir. Therefore by choosing w to be close to H the liquid is forced to remain in the reservoir and not spontaneously flow back into the loading opening. This pressure difference is initially overcome by the positive displacement pipetting action, to fill the reservoir with the liquid.

FIG. 7 also illustrates steps for dispensing a droplet. In the specific embodiment illustrated, droplet dispensing from an on-chip reservoir occurs in the following steps. In Step A, the reservoir electrode is activated. In Step B, a liquid column is extruded from the reservoir by activating a series of electrodes adjacent to it. Once the column overlaps the electrode on which the droplet is to be formed. In Step C, all the remaining electrodes are deactivated to form a neck in the column. In Step D, simultaneously or subsequently to Step C, the reservoir electrode is activated to pull the liquid back causing the neck to break completely and form a droplet.

Though simple in principle, the reliability and repeatability of the dispensing process is affected by several design and experimental parameters. The design parameters include the reservoir shape and size, shape and size of the pull-back electrode, size of the unit electrode (and correspondingly the unit droplet) and the spacer thickness. In one embodiment, the design parameters may be established as follows: The electrode size may be fixed, e.g., at about 500 µm, and most of the other design parameters were chosen using this as the starting point. Droplet dispensing for a water-silicone oil system may be suitably conducted using a droplet aspect ratio (diameter/height) greater than 5 and a water-air system may be suitably conducted using a an aspect ratio greater than 10. Thus, given an approximately 500 µm electrode size, the spacer thickness may be about 100 µm for a nominal droplet diameter of 500 µm. For this electrode size and spacer thickness combination the unit droplet volume is expected to be between about 25 and 50 nL. Larger aspect ratios caused droplets to split easily even while transporting. As a rule of thumb, an aspect ratio between about 4 and about 6 is most optimal for droplet transport, dispensing and splitting for an electrowetting system in silicone oil.

The reservoir size is essentially determined by the smallest pipette-loadable volume on the lower end and chip real-estate concerns on the higher end. In theory, the reservoirs could be made as large as possible and always filled with a smaller quantity of liquid as needed. In some embodiments, reservoir capacities may vary from about 500 to about 1500 nL.

A tapering pull-back electrode (wider at the dispensing end) may be employed in some embodiments to ensure that the liquid stays at the dispensing end of the reservoir as the reservoir is depleted.

In addition to the design parameters discussed above there are additional experimental factors which affect dispensing, and these include the volume of liquid in the reservoir, the length of the extruded liquid column and the voltage applied. It is generally observed that the volume variation is much higher for the last few droplets generated from a reservoir i.e. when the reservoir is close to being empty. The length of the extruded column also determines the volume of a unit droplet. During the necking process the liquid in the extruded column drains with half the volume going towards the reservoir and another half towards the droplet. Therefore the longer the extruded finger the larger the droplet volume. The volume variation is also larger when the droplet is formed farther away from the reservoir. The extruded liquid column also determines the minimum unusable dead volume in the reservoir.

The invention provides droplet actuators and associated systems configured for loading one or more droplet fluids by displacement of filler fluid. The invention also provides methods of making and using such droplet actuators.

In some cases, the droplet fluid loading approach of the invention relies on displacement of filler fluid in order to move a droplet fluid from a locus which is exterior to the gap to a locus which is inside the gap and/or from one portion of the gap to another. In one embodiment, the droplet fluid loading operation moves a droplet fluid from a position in which the droplet is not subject to droplet operations to a locus in which the fluid is subject to droplet operations. For example, a droplet fluid loading operation of the invention may be employed to move a droplet fluid from a locus in which the droplet fluid is not subject to electrode-mediated droplet operations into a locus in which the droplet fluid is subject to electrode-mediated droplet operations. In a specific example, an aliquot of droplet fluid may be transported into proximity with electrodes configured to dispense droplets of the droplet fluid, and the electrode arrangement may be used to dispense such droplets and may further be used to transport such droplets to downstream droplet operations, e.g. for conducting an assay.

Various droplet fluid loading purchase of the invention work well for any droplet fluid volume, including small droplet fluid volumes; reduce, preferably entirely eliminate, the possibility of introducing air into the droplet actuator during loading; and reduce, preferably entirely eliminate, dead volume of droplet fluid.

Figure 8A:
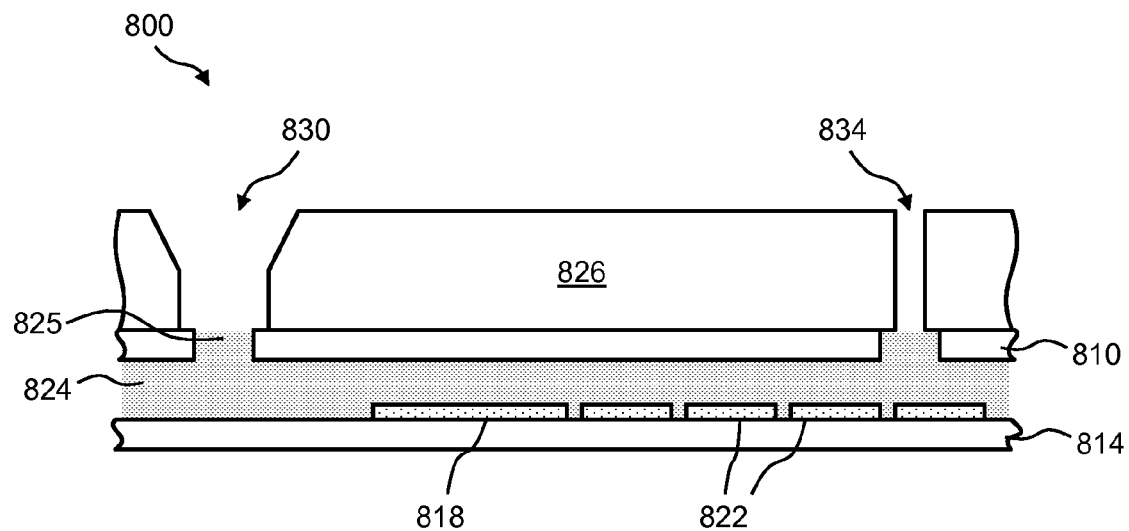
FIGS. 8A and 8B illustrate a side view and top view (not to scale), respectively, of a droplet actuator configured to make use of negative displacement of filler fluid for droplet fluid loading.
Figure 8B:
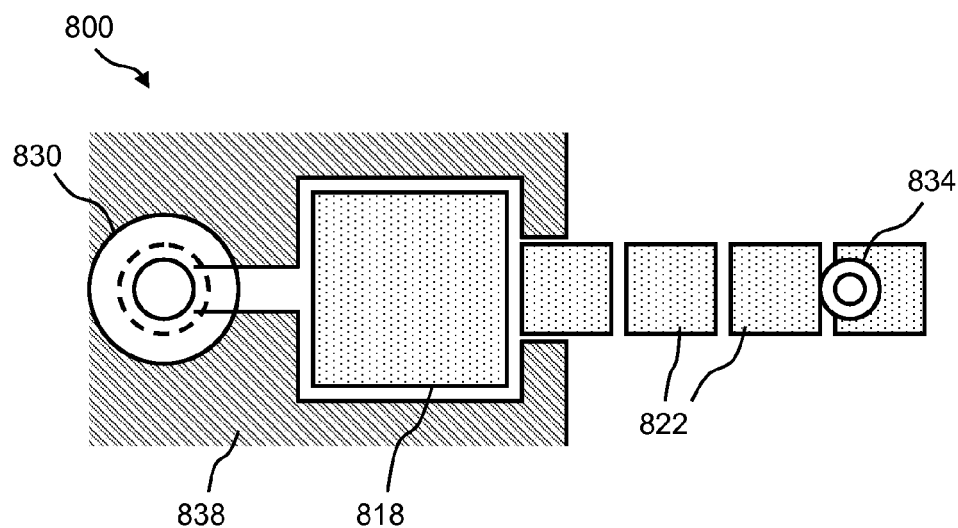

FIGS. 8A and 8B illustrate a side view and top view (not to scale), respectively, of a droplet actuator 800. Droplet actuator 800 is configured to make use of negative displacement of filler fluid for droplet fluid loading. Droplet actuator 800 includes a top substrate 810 and a bottom substrate 814 arranged to provide a gap for conducting droplet operations. A reservoir electrode 818 and a set of electrodes 822 (e.g., droplet operations electrodes) are provided in association with bottom substrate 814. The gap between top substrate 810 and a bottom substrate 814 is filled with a volume of filler fluid 824.

A loading assembly 826 is provided atop top substrate 810, as illustrated in FIG. 8A. It will be appreciated that top substrate 810 and loading assembly 826 (as well as other loading assemblies described herein) may be a single structure comprising some or all elements of top substrate 810 and loading assembly 826.

Loading assembly 826 includes a droplet fluid reservoir 830 that substantially aligns with an inlet opening 825 of top substrate 810. Droplet fluid reservoir 830 is configured to receive a volume of droplet fluid (not shown), which is to be loaded into the gap of droplet actuator 800. Loading assembly 826 may also include a negative pressure opening 834 that substantially aligns with an outlet opening of top substrate 810. Negative pressure opening 834 is configured to receive a volume of filler fluid 824 that is displaced during loading of the droplet fluid.

FIG. 8B illustrates gasket 838 arranged to direct droplet fluid (not shown) from droplet fluid reservoir 830 toward reservoir electrode 818 during a fluid loading operation. Reservoir 830 is located a certain distance from reservoir electrode 818 in order to hinder or restrain droplet fluid (not shown) from retreating back into droplet fluid reservoir 830 once loaded into droplet actuator 800. Additional aspects of droplet actuator 800 in use are described with reference to FIGS. 9A, 9B, and 9C.

FIG. 9A illustrates a side view of droplet actuator 900 (not to size) with droplet fluid reservoir 930 being loaded with droplet fluid. A droplet fluid source 950, such as a pipette or syringe, may be used to deposit a volume of droplet fluid 954 into droplet fluid reservoir 930. A negative pressure device 958 (not to size), such as, but not limited to, a syringe, pipette, or pump, may be securely fitted to negative pressure opening 934. The size of negative pressure opening 934 may be selected to couple the opening to a negative pressure device 958, e.g., the tip of a pipette, syringe, or other negative pressure device or coupling for a negative pressure device, such as a capillary tube. Initially, negative pressure device 958 is in a state of applying little or no significant negative pressure to filler fluid 924, as illustrated in FIG. 9A, and droplet fluid 954 is retained in droplet fluid reservoir 930.

FIG. 9B illustrates a side view of droplet actuator 900 during a droplet fluid loading operation using negative pressure device 958. Negative pressure is applied to filler fluid 924 using negative pressure device 958. Droplet fluid 954 flows from droplet fluid reservoir 930 through opening 925 (shown in FIG. 9A), into droplet actuator 900, and toward reservoir electrode 918. The negative pressure device forces a volume of filler fluid 924 out of the gap, and the displaced filler fluid is replaced by a volume of droplet fluid 954. This action continues until a desired volume of droplet fluid 954 is drawn into sufficient proximity with reservoir electrode 918 to permit reservoir electrode 918 to be used to conduct one or more electrode-mediated droplet operations. As illustrated in FIG. 9C, reservoir electrode 918 may be activated to induce loaded fluid to move into a locus which is generally atop the reservoir electrode 918.

FIG. 9C illustrates a side view of droplet actuator 900 following the droplet fluid loading operation. A slug of droplet fluid 954 is positioned atop reservoir electrode 918. A volume of filler fluid 924 has been removed from the gap due to the action of negative pressure device 958.

FIG. 10A illustrates a side view (not to scale) of a droplet actuator 1000 that makes use of negative displacement for droplet fluid loading. Droplet actuator 1000 is substantially the same as droplet actuator 1000 that is described in FIG. 8, except that the negative pressure opening and the negative pressure device of loading assembly 1026 is constituted by a threaded negative pressure opening 1010 that has a screw 1014 therein. The action of backing screw 1014 out of threaded negative pressure opening 1010 creates negative pressure (i.e., vacuum pressure). FIG. 10A illustrates screw 1014 substantially fully engaged within threaded negative pressure opening 1010 and a volume of droplet fluid 1054 present in droplet fluid reservoir 1030. Screw 1014 may be backed out of threaded negative pressure opening 1010 to force a volume of filler fluid 1024 out of the gap. The displaced filler fluid 1024 is replaced by droplet fluid 1054 as it is drawn into droplet actuator 1000.

FIG. 10B illustrates a side view of droplet actuator 1000 with the droplet fluid loading operation complete. More specifically, FIG. 10B illustrates a slug of droplet fluid 1054 atop reservoir electrode 1018 and a volume of filler fluid 1024 that is present within threaded negative pressure opening 1010 due to the action of backing out screw 1014, which creates a negative pressure (i.e., vacuum pressure).

Referring again to FIG. 8, loading assembly 1026, which may include any of the active negative pressure mechanisms, may be permanently attached to the droplet actuator or, alternatively, may be attached to the droplet actuator during droplet fluid loading only and then removed.

FIG. 11A illustrates a side view (not to scale) of a droplet actuator 1100. Droplet actuator 1100 is substantially the same as the droplet actuator that is described in FIGS. 8 and 9, except that the negative pressure opening and the negative pressure device of loading assembly 1126 is replaced with a negative pressure opening 1110 that has a septum 1114 therein. Septum 1114 is configured to seal negative pressure opening 1110 and is formed of a material that is suitable for sealing, that is resistant to the filler fluid, and that may be easily punctured. For example, septum 1114 may be formed of any rubbery material, such as elastomer material. Atop septum 1114 is an absorbent material 1118, which may be any material that is suitable for absorbing filler fluid 1124 and that may be easily punctured. For example, absorbent material 1118 may be a sponge material or foam material.

In operation, a volume of droplet fluid 1154 is deposited into droplet fluid reservoir 1130, as illustrated in FIG. 11A. Subsequently, septum 1114 and absorbent material 1118 are punctured in a manner to form a capillary 1122 between filler fluid 1124 in the gap of droplet actuator 1100 and absorbent material 1118, as illustrated in FIG. 11B. In this way, due to negative pressure created by capillary 1122, which is displacing filler fluid 1124 into absorbent material 1118, droplet fluid 1154 displaces filler fluid 1124 as it is pulled into sufficient proximity with reservoir electrode 1118 such that reservoir electrode 1118 may be employed to conduct one or more droplet operations using droplet fluid 1154.

FIG. 11B illustrates a side view of droplet actuator 1100 with the droplet fluid loading operation complete. More specifically, FIG. 11B illustrates a slug of droplet fluid 1154 atop reservoir electrode 1118 and a volume of filler fluid 1124 that is present within capillary 1122 and absorbent material 1118 due to the creation of negative pressure when septum 1114 and absorbent material 1118 are punctured.

Referring again to FIG. 11B, droplet fluid reservoir 1130 has a diameter D, the gap of droplet actuator 1100 has a height h, and capillary 1122 has a diameter d. In order to create the desired pressure differentials along droplet actuator 1100 that best encourages fluid flow from droplet fluid reservoir 1130 to capillary 1122, D>h>d.

FIG. 12A illustrates a side view (not to scale) of a droplet actuator 1200. Droplet actuator 1200 makes use of a passive method of filler fluid displacement for droplet fluid loading. Droplet actuator 1200 is substantially the same as the droplet actuator that is described in FIGS. 8 and 9, except that the negative pressure opening of loading assembly 1226 that has the negative pressure device installed therein is replaced with a capillary 1210 and no mechanism installed therein.

Additionally, droplet fluid reservoir 1230 has a diameter D, the gap of droplet actuator 1200 has a height h, and capillary 1210 has a diameter d. In order to create the desired pressure differentials along droplet actuator 1200 that promote fluid flow by capillary forces from droplet fluid reservoir 1230 into capillary 1210, D>h>d.

The capillary 1210 is sealed using tape for example (not shown) before fluid loading and air is trapped within the capillary. In operation, when a volume of droplet fluid 1254 is loaded into droplet fluid reservoir 1230, and the seal is removed, the capillary action of capillary 1210 pulls filler fluid 1224 therein and creates a negative pressure that allows a slug of droplet fluid 1254 to move into droplet actuator 1200 and displace filler fluid 1224.

FIG. 12B illustrates a side view of droplet actuator 1200 with the droplet fluid loading operation complete. More specifically, FIG. 12B illustrates a slug of droplet fluid 1254 atop reservoir electrode 1218 and a volume of filler fluid 1224 that is present within capillary 1210 due to the creation of negative pressure via capillary 1210.

FIGS. 13A and 13B illustrate a side view and top view (not to scale), respectively, of a droplet actuator 1300. Droplet actuator 1300 is formed of a top substrate 1310 and a bottom substrate 1314, with a gap therebetween. A reservoir electrode 1318 and a set of electrodes 1322 (e.g., droplet operations electrodes) are provided on bottom substrate 1314. The gap between top substrate 1310 and bottom substrate 1314 is filled with a volume of filler fluid 1326. Additionally, top substrate 1310 includes a fluid reservoir 1330 that substantially aligns with an inlet opening of top substrate 1310, which is near reservoir electrode 1318. Fluid reservoir 1330 is configured to receive a volume of droplet fluid 1334, which is to be loaded into droplet actuator 1300. Top substrate 1310 also includes one or more vent holes 1338, which is disposed along electrodes 1322 and near a spacer 1342 that is between top substrate 1310 and bottom substrate 1314.

Additionally, the one or more vent holes 1338 are sealed by a seal 1344. In one example, seal 1344 may be a removable seal. In another example, seal 1344 may be a seal that may be punctured, such as a seal that is formed of any rubbery material (e.g., elastomer material) or foil material. In any case, seal 1344 is formed of a material that is resistant to the filler fluid. Furthermore, FIGS. 13A and 13B show a volume of air 1350 that is trapped is in the gap of droplet actuator 1300, and at the one or more vent holes 1338.

In operation, prior to loading filler fluid 1326 into droplet actuator 1300, the one or more vent holes 1338, which are negative pressure holes, are sealed via seal 1344. With vent holes 1338 sealed, droplet actuator 1300 is then loaded with filler fluid 1326, which causes a volume of air 1350 to be trapped in the gap, against spacer 1342 and at vent holes 1338, as illustrated in FIGS. 13A and 13B. Air 1350 is trapped under pressure because there is no path for venting air 1350 out of droplet actuator 1300. The volume of air 1350 may be controlled, for example, by the placement of the one or more vent holes 1338 and/or by the geometry of spacer 1342. Droplet fluid 1334 is present in fluid reservoir 1330, which is sealed with seal 1347. Thus, the contents of the droplet actuator are under pressure. In order to load droplet fluid 1334 into droplet actuator 1300, seal 1344 is breached (e.g., removed, broken or punctured) which permits pressurized air 1350 to escape through vent holes 1338, which causes droplet fluid 1334 to displace filler fluid 1326 as it flows into the one or more vent holes 1338. This action pulls a slug of droplet fluid 1334 onto reservoir electrode 1318 (not shown).

Additionally, fluid reservoir 1330 has a diameter D, the gap of droplet actuator 1300 has a height h, and vent holes 1338 have a diameter d. In order to create the desired pressure differentials along droplet actuator 1300 that best encourage fluid flow from fluid reservoir 1330 to vent holes 1338, D>h>d.

Various kinds of pressure sources, positive and/or negative, may be used to cause dislocation of filler fluid to result in the desired dislocation or movement of droplet fluid, e.g., vacuum pump, syringe, pipette, capillary forces, and/or absorbent materials. For example, negative pressure may be used to dislocate filler fluid and thereby move a droplet fluid from a locus which is exterior to the gap to a locus which is inside the gap and/or from one portion of the gap to another. The pressure source may be controlled via active and/or passive mechanisms. Displaced filler fluid may be moved to another locus within the gap and/or transported out of the gap. In one embodiment, displaced filler fluid flows out of the gap, while a droplet fluid flows into the gap and into proximity with a droplet operations electrode.

For examples of fluids that may be subjected to droplet operations using the electrode designs and droplet actuator architectures of the invention, see International Patent Application No. PCT/US 06/47486, entitled, "Droplet-Based Biochemistry," filed on Dec. 11, 2006. In some embodiments, the fluid includes a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, fluidized tissues, fluidized organisms, biological swabs and biological washes. In other embodiments, the fluid may be a reagent, such as water, deionized water, saline solutions, acidic solutions, basic solutions, detergent solutions and/or buffers. In still other embodiments, the fluid includes a reagent, such as a reagent for a biochemical protocol, such as a nucleic acid amplification protocol, an affinity-based assay protocol, a sequencing protocol, and/or a protocol for analyses of biological fluids.

The foregoing detailed description of embodiments refers to the accompanying drawings, which illustrate specific embodiments of the invention. Other embodiments having different structures and operations do not depart from the scope of the present invention. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation, as the present invention is defined by the claims as set forth hereinafter.

We claim:

1. A droplet actuator comprising a substrate comprising:
    (a) a path of two or more droplet operations electrodes configured for conducting one or more droplet operations; and
    (b) dedicated reference electrodes arranged alongside the path and inset into and/or interdigitated with one or more droplet operations electrodes.

2. The droplet actuator of claim 1 comprising a reference electrode inset into a droplet operations electrode.

3. The droplet actuator of claim 1 comprising a reference electrode inset between two or more droplet operations electrodes.

4. The droplet actuator of claim 1 comprising a reference electrode interdigitated with a droplet operations electrode.

Figure 5A:
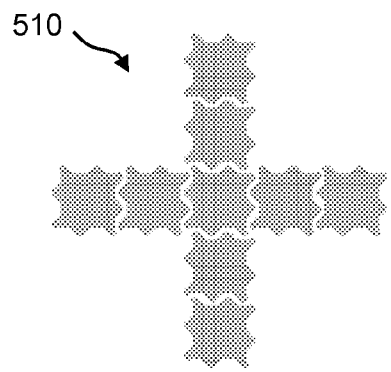
FIGS. 5A, 5B, 5C, 5D and 5E illustrate electrode patterns in which the electrodes are overlapping, but not interdigitated, in order to facilitate droplet overlap with adjacent electrodes.

5. The droplet actuator of claim 1 having a droplet operations electrode configuration as shown in FIG. 5A.

Figure 5B:
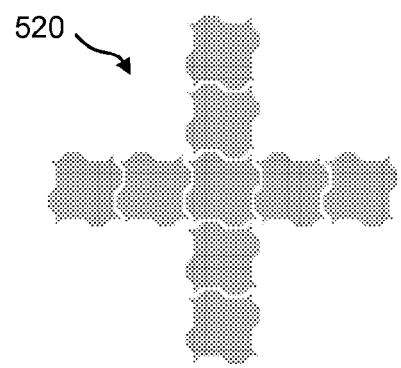

6. The droplet actuator of claim 1 having a droplet operations electrode configuration as shown in FIG. 5B.

Figure 5C:
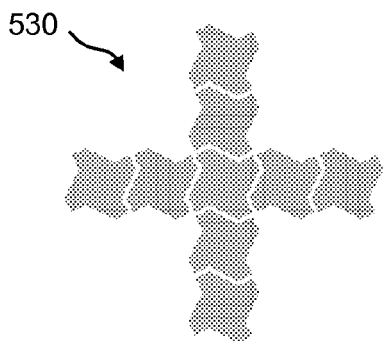

7. The droplet actuator of claim 1 having a droplet operations electrode configuration as shown in FIG. 5C.

Figure 5D:
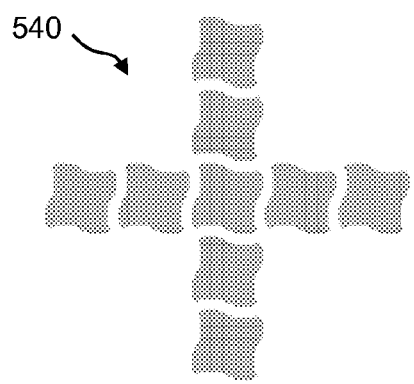

8. The droplet actuator of claim 1 having a droplet operations electrode configuration as shown in FIG. 5D.

Figure 5E:
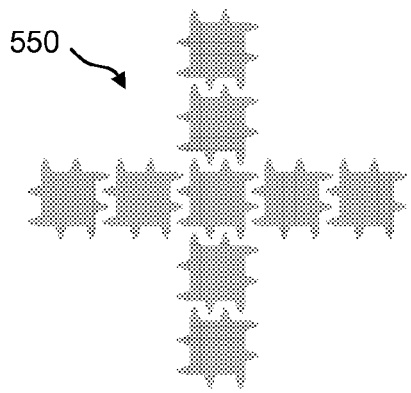

9. The droplet actuator of claim 1 having a droplet operations electrode configuration as shown in FIG. 5E.

10. The droplet actuator of claim 1 wherein the droplet operations electrode configuration comprises an electrode that is rotationally but not reflectively symmetrical.

11. The droplet actuator of claim 1 wherein the droplet operations electrode configuration comprises a path and/or array of the electrodes.

12. The droplet actuator of claim 1 wherein the droplet operations electrode configuration comprises interdigitated electrodes.

13. The droplet actuator of claim 1 wherein the droplet operations electrode configuration comprises electrodes that are not interdigitated.

14. The droplet actuator of claim 1 wherein the droplet operations electrode configuration comprises electrodes having X-fold rotational symmetry, wherein X is 3.

15. The droplet actuator of claim 1 wherein the droplet operations electrode configuration comprises electrodes having X-fold rotational symmetry, wherein X is 4.

16. The droplet actuator of claim 1 wherein the droplet operations electrode configuration comprises electrodes having X-fold rotational symmetry, wherein X is 5.

17. The droplet actuator of claim 1 wherein the droplet operations electrode configuration comprises electrodes having X-fold rotational symmetry, wherein X is 6.

18. The droplet actuator of claim 1 wherein the droplet operations electrode configuration comprises electrodes having X-fold rotational symmetry, wherein X is 7.

19. The droplet actuator of claim 1 wherein the droplet operations electrode configuration comprises electrodes having X-fold rotational symmetry, wherein X is 8.

20. The droplet actuator of claim 1 wherein the droplet operations electrode configuration comprises electrodes having X-fold rotational symmetry, wherein X is 9.

21. The droplet actuator of claim 1 wherein the droplet operations electrode configuration comprises electrodes having X-fold rotational symmetry, wherein X is 10.

22. The droplet actuator of claim 1 wherein the droplet operations electrode configuration comprises electrodes having X-fold rotational symmetry, wherein X is greater than 10.

23. The droplet actuator of claim 1 wherein the droplet operations electrode configuration comprises a path and/or array of the electrodes, wherein adjacent electrodes are arranged such that no line can be drawn between two adjacent electrodes without overlapping one or both of the two adjacent electrodes.

24. The droplet actuator of claim 23 wherein the electrodes are not interdigitated.

25. The droplet actuator of claim 23 wherein the electrodes are interdigitated.

26. The droplet actuator of claim 1 wherein the droplet operations electrode configuration comprises an electrode that is rotationally and reflectively symmetrical, where the rotational symmetry is X-fold and X is 5, 6, 7, 8, 9, 10 or more.

27. The droplet actuator of claim 1 wherein the droplet operations electrode configuration comprises a path and/or array of interdigitated electrodes, wherein adjacent interdigitated electrodes are arranged such that no line can be drawn between two adjacent electrodes without overlapping one or both of the two adjacent electrodes.

28. The droplet actuator of claim 1 wherein the droplet operations electrode configuration comprises a path or array of electrodes, each having a shape that is a section of rotationally and reflectively symmetrical shape, the electrode having X-fold rotational symmetry, where X is 5, 6, 7, 8, 9, or more.

29. The droplet actuator of claim 1 wherein the droplet operations electrode configuration comprises a path or array of electrodes, each having a shape that comprises a section of a rotationally but not reflectively symmetrical shape, the electrode having X-fold rotational symmetry, where X is 5, 6, 7, 8, 9, 10 or more.

* * * * *